United States Patent
Lee et al.

(10) Patent No.: US 11,680,282 B2
(45) Date of Patent: Jun. 20, 2023

(54) APPARATUS AND METHOD FOR DISTINGUISHING ANTIBIOTICS SUSCEPTIBILITY

(71) Applicant: ACCUNOSE CO.,LTD., Gyeonggi-do (KR)

(72) Inventors: Won Il Lee, Gyeonggi-do (KR); Young Hyeon Park, Gyeonggi-do (KR)

(73) Assignee: ACCUNOSE CO., LTD., Gyeonggi-Do (KR)

( * ) Notice: Subject to any disclaimer, the term of this patent is extended or adjusted under 35 U.S.C. 154(b) by 191 days.

(21) Appl. No.: 17/386,687

(22) Filed: Jul. 28, 2021

(65) Prior Publication Data

US 2022/0205013 A1 Jun. 30, 2022

(30) Foreign Application Priority Data

Dec. 28, 2020 (KR) ........................ 10-2020-0184547

(51) Int. Cl.
| | | |
|---|---|---|
| *C12Q 1/00* | (2006.01) | |
| *C12Q 1/18* | (2006.01) | |
| *C12N 1/20* | (2006.01) | |
| *G01N 1/38* | (2006.01) | |
| *G01N 1/34* | (2006.01) | |
| *C12M 1/32* | (2006.01) | |
| *C12M 1/12* | (2006.01) | |
| *G01N 21/64* | (2006.01) | |

(52) U.S. Cl.
CPC ............. *C12Q 1/18* (2013.01); *C12M 23/12* (2013.01); *C12M 25/16* (2013.01); *C12N 1/20* (2013.01); *G01N 1/34* (2013.01); *G01N 1/38* (2013.01); *G01N 21/6428* (2013.01); *C12N 2523/00* (2013.01); *G01N 2021/6439* (2013.01)

(58) Field of Classification Search
CPC ....................................................... C12Q 1/18
See application file for complete search history.

(56) References Cited

U.S. PATENT DOCUMENTS

| | | |
|---|---|---|
| 2017/0211121 A1 | 7/2017 | Stern et al. |
| 2018/0088141 A1 | 3/2018 | Vacic et al. |
| 2018/0284146 A1 | 10/2018 | Hansen et al. |
| 2019/0128910 A1 | 5/2019 | Vacic et al. |
| 2020/0149086 A1 | 5/2020 | Stern et al. |
| 2021/0116471 A1 | 4/2021 | Hansen et al. |

FOREIGN PATENT DOCUMENTS

| | | |
|---|---|---|
| JP | 2019-515311 A | 6/2019 |
| JP | 2020-504610 A | 2/2020 |
| KR | 10-2003-0003576 A | 1/2003 |
| KR | 10-20106-0043827 A | 4/2016 |
| KR | 101776698 B1 | 9/2017 |
| KR | 10-2018-0048456 A | 5/2018 |
| KR | 10-2019-0142555 A | 12/2019 |
| WO | 2018/119439 A1 | 6/2018 |
| WO | 2020/073016 A1 | 4/2020 |

OTHER PUBLICATIONS

International Search Report for corresponding International Application No. PCT/KR2021/008915 dated Oct. 19, 2021.

*Primary Examiner* — Albert M Navarro
(74) *Attorney, Agent, or Firm* — Pearne & Gordon LLP (57) ABSTRACT

A method of testing an antibiotic susceptibility includes dispensing and cultivating sample solution into culture wells including one or more comparative wells and a plurality of antibiotic wells receiving two or more kinds of antibiotics, respectively, receiving the sample solution into a plurality of preprocessing wells each including magnetic particles and fluorescent particles that bond to one or more kinds of bacteria such that the bacteria and the magnetic particles and fluorescent particles bond to each other, receiving the sample solution into a plurality of image wells having magnetic members thereunder such that the magnetic particles bonding to the bacteria are arranged on the bottoms of the image wells, removing the sample solution from the image wells that have undergone the planarizing step, taking fluorescent images of the image wells washed in the washing step, and determining an antibiotic tolerance/susceptibility of the sample solution by analyzing the fluorescent images.

12 Claims, 6 Drawing Sheets

FLUORESCENT SIGNAL

[Fig. 6B]

FLUORESCENT SIGNAL

[Fig. 6C]

FLUORESCENT SIGNAL

APPARATUS AND METHOD FOR DISTINGUISHING ANTIBIOTICS SUSCEPTIBILITY

CROSS REFERENCE TO RELATED APPLICATION

The present application claims priority to Korean Patent Application No. 10-2020-0184547, filed Dec. 28, 2020, the entire contents of which is incorporated herein for all purposes by this reference.

TECHNICAL FIELD

The present disclosure relates to a test apparatus and method for determining whether infectious bacteria have a tolerance/susceptibility to an antibiotic, that is, an apparatus and method for testing an antibiotic susceptibility that can quickly determine whether infectious bacteria propagate against various antibiotics, depending on a respective susceptibility.

BACKGROUND

In general, an antibiotic susceptibility test is for estimating the effect of antibiotics by checking whether there is a tolerance to an antibiotic to be used for infectious disease treatment, and an antibiotic susceptibility test is performed to prescribe appropriate antibiotics. Antibiotic susceptibility is the self-defense ability of bacteria that is obtained to defend themselves against antibiotics, and bacteria having a tolerance against specific antibiotics propagate without being influenced by the antibiotics, so infectious disease treatment is impossible in this case. Accordingly, it is required to prescribe appropriate antibiotics through an antibiotic susceptibility test, whereby it is possible to reduce side effects due to misuse and abuse of antibiotics.

Such an antibiotic susceptibility test determines whether bacteria propagate, depending on whether the bacteria have a tolerance to each antibiotic. When bacteria divide several times in a liquid media at a room temperature, make a group in a predetermined time, and absorbance changes, it is possible to determine whether there is susceptibility to an antibiotic on the basis of the absorbance. That is, such an antibiotic susceptibility test can determine susceptibility when standing by until bacteria make a group and absorbance changes, so the test takes over one day.

A method such as polymerase chain reaction that can test susceptibility to an antibiotic within short time has been developed to reduce the test time for antibiotic susceptibility, but there is a defect that expensive equipment and professional workers are required.

A technology about antibiotic susceptibility test equipments has been disclosed in Korean Patent No. 10-2001-0039493 in the related art, the entire contents of which is incorporated herein for all purposes by this reference.

SUMMARY

The present disclosure has been made in an effort to solve the problems described above and an objective of the present disclosure is to provide an apparatus and method for testing antibiotic susceptibility, the apparatus and method replacing professional workers and being able to quickly and accurately perform an antibiotic susceptibility test.

In order to achieve the objectives of the present disclosure, a method of testing antibiotic susceptibility includes: a cultivating step of dispensing and cultivating sample solution into culture wells including one or more comparative wells and a plurality of antibiotic wells receiving two or more kinds of antibiotics, respectively; a preprocessing step of receiving the sample solution, which has been cultivated in the cultivating step, into a plurality of preprocessing wells each including magnetic particles and fluorescent particles that bond to one or more kinds of bacteria such that the bacteria and the magnetic particles and fluorescent particles bond to each other; a planarizing step of receiving the sample solution, which has undergone the preprocessing step, into a plurality of image wells having magnetic members thereunder such that the magnetic particles bonding to the bacteria are arranged on the bottoms of the image wells; a washing step of removing the sample solution from the image wells that have undergone the planarizing step; an imaging step of taking fluorescent images of the image wells washed in the washing step; and an analyzing step of determining antibiotic a tolerance/susceptibility of the sample solution by analyzing the fluorescent images taken in the imaging step.

The method of testing antibiotic susceptibility may further include a sample homogenizing step of homogenizing the sample solution by repeatedly pipetting the sample solution using a plurality of pipets.

The cultivating step may include a culture heat applying step of applying heat at 35 to 40 degrees to the culture wells, and may cultivate the sample solution dispensed in the culture wells for 60 to 90 minutes.

The method of testing antibiotic susceptibility may include: a primary transfer step of transferring the sample solution cultivated in the culture wells to the preprocessing wells using a plurality of pipets; and a secondary transfer step of transferring the sample solution in the preprocessing wells to the image wells, respectively, using the pipets.

The washing may include: a sample solution removal step of removing top sample solution in the image wells that have undergone the planarizing; and a washing solution supply step of supplying washing solution from a plurality of washing wells having washing solution to the image wells with the top sample solution removed through the sample solution removal step.

The analyzing step may include: an image analyzing step of finding out the number of fluorescent signals of fluorescent images taken in the imaging step; and an antibiotic analyzing step of determining an antibiotic tolerance/susceptibility of the sample solution on the basis of the number of the fluorescent signals analyzed in the image analyzing step.

The method of testing antibiotic susceptibility may further include a specific bacteria-fluorescence bonding step of bonding the bacteria in the sample solution to secondary fluorescent particles.

An apparatus for testing antibiotic susceptibility according to another embodiment of the present disclosure includes: a sample solution supplier; a culture line composed of three or more rows of culture wells that receive sample solution from the sample solution supplier and include one or more comparative wells and a plurality of antibiotic wells having two or more antibiotics, respectively; a preprocessing line composed of a plurality of preprocessing wells that receives sample solution cultivated in the culture wells, is provided in the same number as or more than the culture wells, and each has fluorescent particles and magnetic particles; an image line composed of a plurality of image wells that receives the sample solution in the preprocessing line and is provided in the same number as or more than the culture wells; a magnetic member disposed under the image line; and an imager imaging the fluorescent particles in the image wells.

The apparatus for testing antibiotic susceptibility may include a transfer module disposed to be movable over the sample solution supplier, the culture line, the preprocessing line, and the image line, and composed of a plurality of pipets moving sample solution by reciprocating up and down.

The transfer module may include: a guide rail installed over the sample solution supplier, the culture line, the preprocessing line, and the image line; a pipet frame moving with an end coupled to the guide rail; a plurality of pipets having a first end coupled to the pipet frame and a second end receiving sample solution; and an operation controller connected to the insides of the pipets and moving sample solution under predetermined pressure.

The culture line may include a heat applier disposed under the culture wells and applying culture heat at a predetermined temperature to the culture wells.

The apparatus for testing antibiotic susceptibility may further include a washing line composed of a plurality of washing wells having washing solution to be transferred to the image wells, respectively, and provided in the same number as or more than the culture wells.

The method and apparatus for testing antibiotic susceptibility according to the present disclosure can determine whether bacteria propagate, which depends on whether the bacteria have an antibiotic tolerance/susceptibility, in the unit of cell through fluorescent images, so it is possible to more quickly derive a result than existing methods that require a long culture time.

Further, the method and apparatus digitize the propagation level of microorganisms, which depends on antibiotics, through fluorescent images, so it is possible to derive an accurate result. Further, the method and apparatus can selectively perform determination for microorganism identification using secondary fluorescent substances that can bond to a specific bacteria.

Further, the apparatus for testing antibiotic susceptibility can replace professional manpower because it is an automated testing apparatus, the use efficiency is high.

BRIEF DESCRIPTION OF THE DRAWINGS

The above and other objectives, features and other advantages of the present invention will be more clearly understood from the following detailed description when taken in conjunction with the accompanying drawings, in which.

DETAILED DESCRIPTION

Hereinafter, exemplary embodiments of the present disclosure will be described with reference to accompanying drawings. The terms and words used in the present specification and claims should not be interpreted as being limited to typical meanings or dictionary definitions, but should be interpreted as having meanings and concepts relevant to the technical scope of the present disclosure based on the rule according to which an inventor can appropriately define the concept of the term to describe most appropriately the best method he or she knows for carrying out the disclosure.

Accordingly, the embodiments described herein and the configurations shown in the drawings are only most preferable embodiments of the present disclosure and do not represent the entire spirit of the present disclosure, so it should be appreciated that there may be equivalents and modifications that can replace the embodiments and the configurations at the time at which the present application is filed.

Hereinafter, embodiments of the present disclosure will be described in detail with reference to the accompanying drawings.

Figure 1:
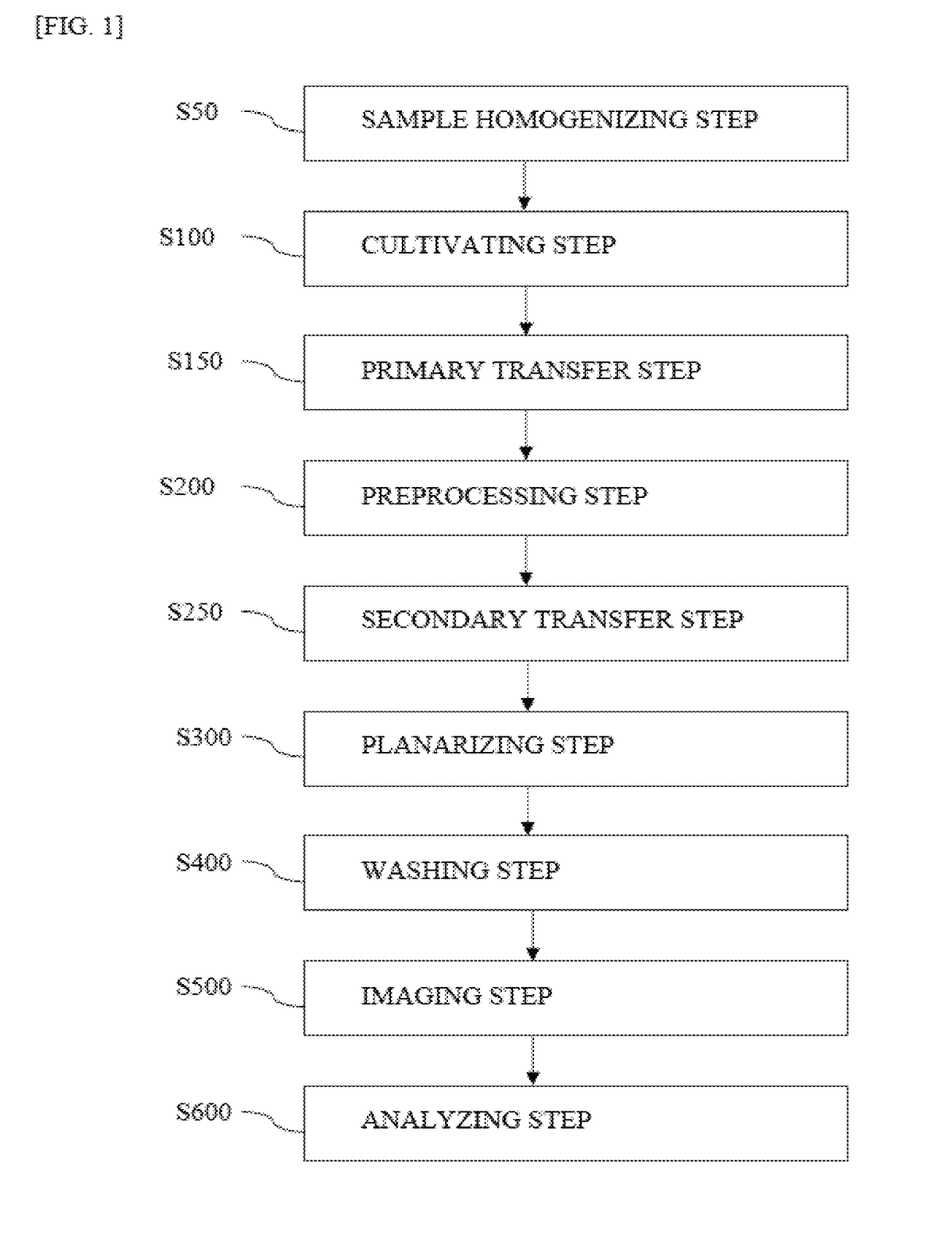
FIG. 1 is an example flowchart of a method of testing an antibiotic susceptibility according to an embodiment of the present disclosure.
Figure 2:
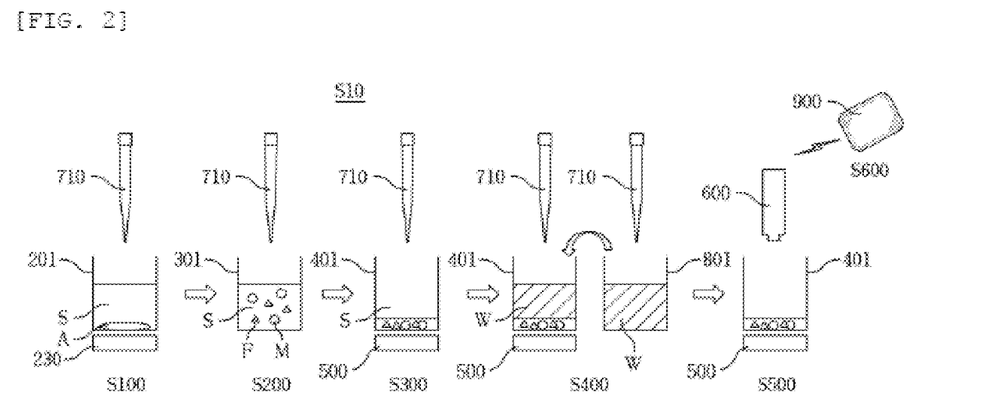
FIG. 2 is a conceptual view schematically showing the principle of the method of testing an antibiotic susceptibility shown in FIG. 1.

Referring to FIGS. 1 and 2, method S10 of testing an antibiotic susceptibility is a method for more quickly and accurately determine a tolerance/susceptibility to various antibiotics A. The method S10 of testing an antibiotic susceptibility of the present disclosure includes: a sample homogenizing step S50, a cultivating step S100, a primary transfer step S150, a preprocessing step S200, a secondary transfer step S250, a planarizing step S300, a washing step S400, an imaging step S500, and an analyzing step S600.

The sample homogenizing step S50 is a step of preparing a sample solution S for an antibiotic tolerance/susceptibility test. The sample homogenizing step S50 prepares a sample solution S by mixing an extracted sample and a culture solution and homogenizes the sample solution by repeatedly pipetting the sample solution S using a plurality of pipets 710. In detail, the sample for an antibiotic tolerance/susceptibility test may be a liquid sample, such as bacteriuria or blood, or pus. Pus may be extracted using a swab and then mixed with a culture solution. The liquid sample, such as bacteriuria and blood, and the culture solution may be mixed at a volume ratio of 9:1, and a drop type sample such as pus extracted using a swab may be mixed with a culture solution at a mass ratio of 9:1. The sample solution S that is a sample-culture solution mixture is put into a sample supplier 100 and mounted in an apparatus 10 for testing an antibiotic susceptibility. It is possible to homogenizing the sample solution S by repeatedly pipetting the sample solution S using a plurality of pipets 710 in the apparatus 10 for testing an antibiotic susceptibility.

The cultivating step S100 is a step for cultivating bacteria in the sample solution S for a predetermined time. The cultivating step S100 receives the sample solution S homogenized in the sample homogenizing step S50. The cultivating step S100 dispenses the sample solution S to culture wells 201 including one or more comparative wells 210 and two or more antibiotic wells 220. Different kinds of antibiotics A are in the antibiotic wells 220 and two or more kinds of antibiotics A may be prepared. That is, the number of the antibiotic wells 220 may correspond to the number of the kinds of antibiotics A, and nine or more antibiotics A may be prepared. The sample solution S may be dispensed with the antibiotics A lyophilized in the antibiotic wells 220. The comparative wells 210 are provided to compare the propagation levels of the bacteria cultivated in the antibiotic wells 220 and the sample solution S may be dispensed to the comparative wells 210 in the same amount as that dispensed to the antibiotic wells 220. The sample solution S may be dispensed by 150-200 µl to each of the comparative wells 210 and the antibiotic wells 220.

The cultivating step S100 may include a culture heat applying step S100A. The culture heat applying step S100A is for applying heat to the culture wells 201, in which the heat of 35 to 40 degrees is applied, thereby being able to provide a condition suitable for cultivating the bacteria in the sample solution S. That is, the cultivating step S100 may cultivate the bacteria by applying heat to the culture wells 201 and may cultivate the dispensed sample solution S for 60 to 90 minutes. In detail, the cultivating step S100 may perform culture for a predetermined time and then homogenize the sample solution by repeatedly pipetting the sample solution using the pipets 710.

The preprocessing step S200 is a step for preprocessing the sample solution S. The preprocessing step S200 supplies and preprocesses the sample solution S in a plurality of preprocessing wells 301. For this step, the sample solution S may be transferred from the primary transfer step S150 and the pipets 710 can transfer the sample solution S cultivated in the culture wells 210 to the preprocessing wells 301, respectively. In this step, the sample solution S may be dispensed by 100-150 µl to each of the preprocessing wells 301. The preprocessing wells 301 includes magnetic particles and fluorescent particles F that bond to one or more kinds of bacteria. That is, in the preprocessing step S200, the sample solution S cultivated in the culture step S100 is transferred to the preprocessing wells 301, whereby the bacteria in the sample solution S, and the magnetic particles M and fluorescent particles F bond to each other. The magnetic particles M and fluorescent particles F may include an antibody that can bond to one or more kinds of bacteria, but the present disclosure is not limited thereto and they may be bonded by an aptamer. In detail, the preprocessing step S200 reacts the bacteria in the sample solution S with the magnetic particles M and fluorescent particles F such that they bond to each other by performing pipetting for about 10 minutes.

The planarizing step S300 planarizes the compound of the bacteria in the preprocessed sample solution S, the magnetic particles M, and the fluorescent particles F, and planarizing is performed in image wells 401. For this step, the sample solution S is transferred from the secondary transfer step S250 and the pipets 710 transfers the sample solution S from the preprocessing wells 301 to the image wells 401, respectively. The sample solution S may be dispensed by 100-150 µl to each of the image wells 401. A magnetic member 500 is disposed under the image well 401, and magnetic particles bonding to the bacteria after the sample solution S is transferred in the preprocessing step S200 are arranged flat on the bottom of the image well 401 by the magnetism of the magnetic member 500. In detail, the planarizing step S300 stands by for a predetermined time after the sample solution S is dispensed, so the magnetic particles can be arranged flat on the bottom. 10 minutes is appropriate for the standby time of the planarizing step S300, but the standby time is not limited thereto and may be appropriately changed, depending on the kinds of bacteria, the size of the image well, the magnetism, and the like.

The washing step S400 is for removing the sample solution S. The washing step S400 removes the sample solution S from the image wells 401. The washing step S400 removes the fluorescent particles not bonding to the bacteria in the sample solution S and other impurities. The washing step S400 includes a sample solution removal step S400A and a washing solution supply step S400B.

The sample solution removal step S400A removes the top sample solution in the image wells 401 that have undergone the planarizing step S300. The sample solution removal step may remove the top sample solution using the pipets 710. In detail, the top sample solution may be removed to the sample supplier 100 by the pipets 710.

The washing solution supply step S400B420 is for supplying a washing solution S to the image wells 401. The washing solution supply step S400B supplies a washing solution W to the image wells 410 with the top sample solution removed in the sample solution removal step S400A. The washing solution W may be provided to a plurality of washing wells 801 and be transferred to the image wells 401 by the pipets 710. The washing solution W may be injected by 100-150 µl to each of the image wells 401. Thereafter, the washing solution supply step S400B may be repeated after the washing solution is removed by the pipets 710 for at least two times.

The imaging step S500 for taking fluorescent images of each of the image wells 401. The imaging step S500 takes fluorescent images of each of the image wells 401 washed in the washing step S400. That is, it is possible to observe fluorescent signals of the fluorescent particles bonding to the bacteria in the sample solution S from the fluorescent images taken by the imaging step S500. In detail, the imaging step S500 uses a fluorescent microscope module and the fluorescent microscope module may automatically focus on the centers of the image wells 401, using auto focusing, and then may take images in a fluorescent mode. The fluorescent microscope module may be movable and may sequentially take images of the image wells 401. In detail, a blue LED may be used for the filter (excitation) of the fluorescent microscope module and a green and red wavelength may be used for an emission filter of the fluorescent microscope module.

The method S10 of testing an antibiotic susceptibility further includes specific bacteria-fluorescence bonding step S700 that bonds the bacteria in the sample solution S to secondary fluorescent particles. In detail, the secondary fluorescent particles may be preserved in the image wells 401 and the sample solution S may be dispensed in the planarizing step S300 with the secondary fluorescent particles preserved in the image wells 401. In the specific bacteria-fluorescence bonding step S700 (not shown), the secondary fluorescent particles bond to a specific bacteria, whereby it is possible to find out the kind of the bacteria through the analyzing step S600. That is, since secondary fluorescent particles bond to an aptamer or an antibody that bonds to a specific bacteria, it is possible to identify the kind of the bacteria according to the positions of the image wells 401.

The analyzing step S600 is for determining an antibiotic tolerance/susceptibility, in which it is possible to determine an antibiotic tolerance/susceptibility to the sample solution S by analyzing the fluorescent images taken in the imaging step S500. The analyzing step S600 includes an image analyzing step S600A, an antibiotic analyzing step S600B, and a bacteria kind-detecting step S600C.

The image analyzing step S600A detects the number of fluorescent signals of the fluorescent images taken in the imaging step S500. The image analyzing step S600A can accurately detect the fluorescent signals through a digital fluorescence counting technology using an image processing algorithm.

The antibiotic analysis step S600B determines an antibiotic tolerance/susceptibility to the sample solution S on the basis of the number of fluorescent signals analyzed in the image analyzing step S600A. In detail, the image analyzing step S600A can distinguish (a) the comparative wells 210 and tolerance wells or (b) susceptibility wells in accordance with the number of the fluorescent signals. When the number of the fluorescent signals of the susceptibility wells is 15% larger than the standard deviation/average of the number of the fluorescent signals of the comparative wells 210 and the tolerance wells, an antibiotic susceptibility is determined. When the number of the fluorescent signals of the comparative wells 210 and the tolerance wells is within 15% of the standard deviation/average, an antibiotic tolerance is determined. When errors during the operation and imaging are partially sensed, the corresponding well might be determined as one having an antibiotic tolerance.

The bacteria kind-detecting step S600C detects the fluorescent signals of the secondary fluorescent particles bonding through the specific bacteria-fluorescence bonding step S700. That is, as the secondary fluorescent particles bond to specific bacteria, the bacteria kind-detecting step S600C can identify the kind of the bacteria according to the positions of the image wells 410 by detecting secondary fluorescent particle signals.

The result of determining a tolerance/susceptibility analyzed through the analyzing step S600 may be displayed on a screen through a computer terminal, and the like. That is, it is possible to show and easily check the determination result of a tolerance/susceptibility and the kind of bacteria in accordance with the position of an antibiotic A in the antibiotic well 220. Further, it may be possible to check the determination result of an antibiotic tolerance/susceptibility through various mobile devices such as a smartphone or a smart pad.

Figure 3:
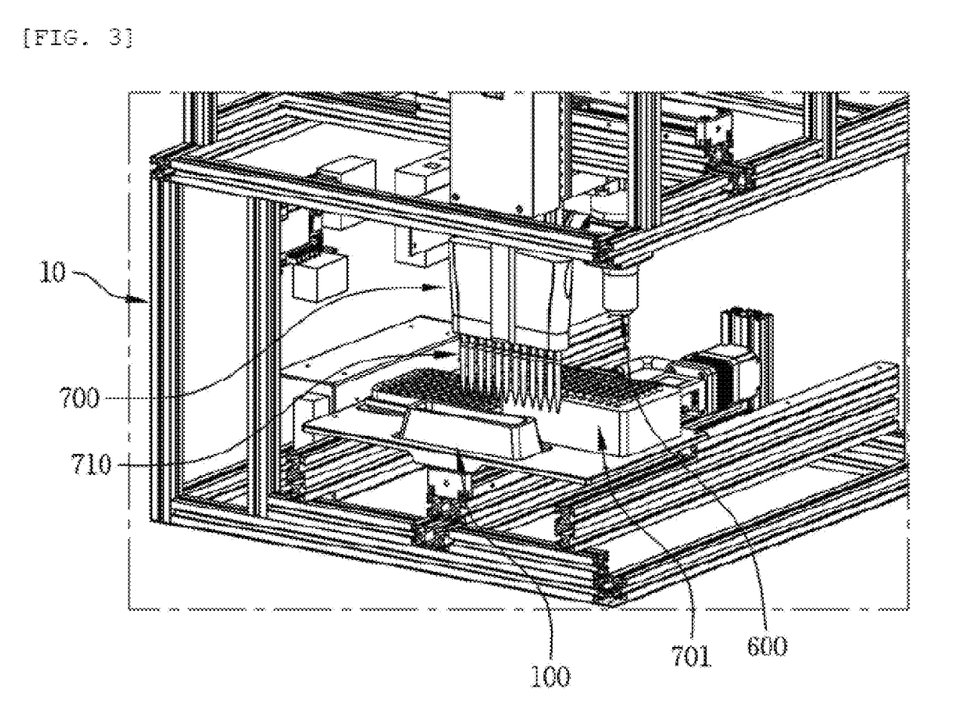
FIG. 3 is a perspective view of an apparatus for testing an antibiotic susceptibility according to the present disclosure.
Figure 4:
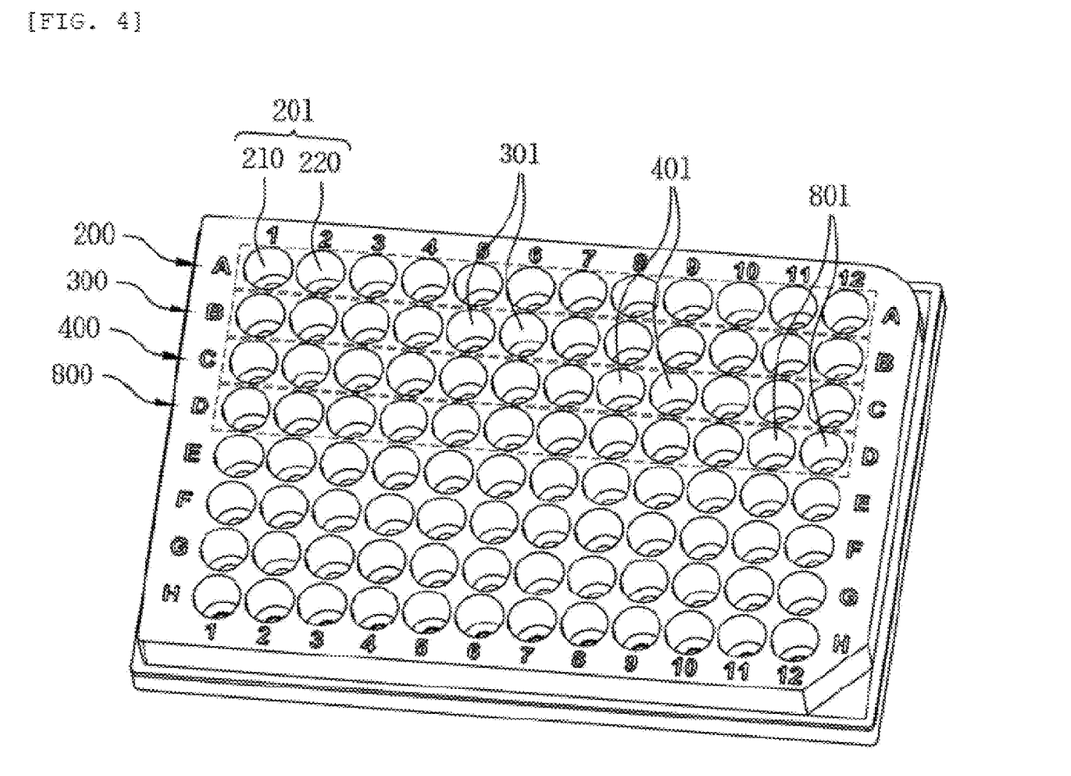
FIG. 4 is a perspective view showing a cultivating line, a preprocessing line, an image line, and a washing line of the apparatus for testing an antibiotic susceptibility shown in FIG. 3.
Figure 5:
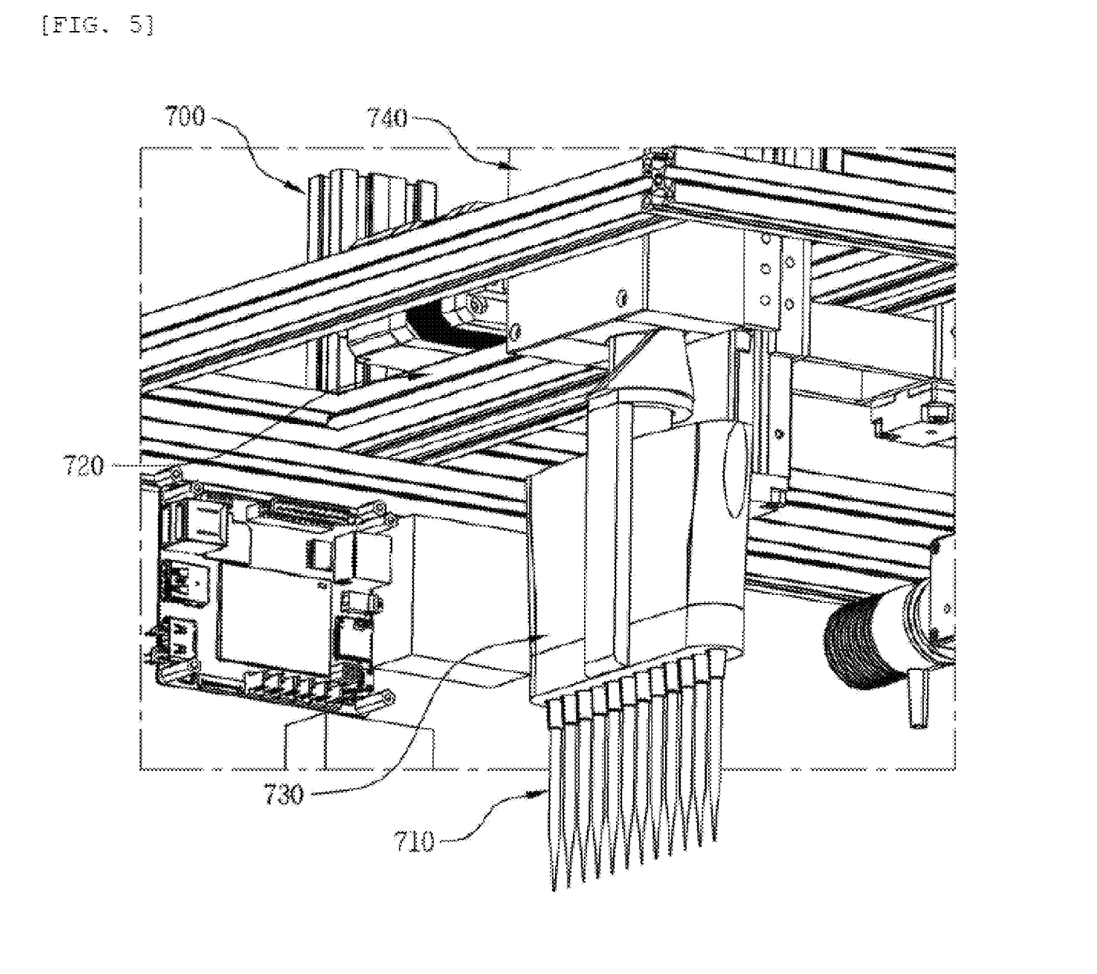
FIG. 5 is a perspective view showing a transfer module of the apparatus for testing an antibiotic susceptibility shown in FIG. 3.

FIGS. 3 to 5 are perspective views showing an apparatus 10 for testing an antibiotic susceptibility of the present disclosure, which is an apparatus for performing the method S10 of testing an antibiotic susceptibility. Next, the configuration of the apparatus 10 for testing an antibiotic susceptibility is described in detail. A method S10 of testing an antibiotic susceptibility using the apparatus 10 for testing an antibiotic susceptibility is the same, so it is not described in detail. The apparatus 10 for testing an antibiotic susceptibility according to the present disclosure includes a sample solution supplier 100, a culture line 200, a preprocessing line 300, an image line 400, a magnetic member 500, an imager 600, a transfer module 700, and a washing line 800.

The sample solution supplier 100 is for preparing sampling solution S. The sample solution supplier 100 homogenizes the sampling solution S to transfer the sampling solution S to the culture line 200. The sample solution supplier 100 may receive sample solution S that is a mixture of an extracted sample and culture solution, and the sample solution applier 100 keeping the sample solution S is mounted in the apparatus 10 for testing an antibiotic susceptibility. The sample solution S kept in the sample solution supplier 100 can be homogenized by the transfer module 700. That is, a plurality of pipets 710 of the transfer module 700 repeatedly pipets the sample solution S in the sample solution supplier 100, thereby homogenizing the sample solution S.

The culture line 200 is for cultivating the bacteria in the sample solution S. The culture line 200 receives the sample solution S from the sample solution supplier 100. The culture line 200 includes one or more comparative wells 210 and two or more antibiotic wells 220, so it is composed of three or more rows of culture wells 201. Bacteria are cultivated without an antibiotic in the comparative well 210, so it is possible to check the number of bacteria propagating in the comparative well 210 as a comparative group. The antibiotic wells 220 receive two or more kinds of antibiotics, respectively, and different kinds of antibiotics A may be provided to the antibiotic wells 220. The number of the antibiotic wells 220 may correspond to the number of the kinds of antibiotics A. Although the culture line 200 is composed of 12 rows, but is not limited thereto and may include antibiotic wells 220 receiving nine or more kinds of antibiotics A and the comparative wells 210. The comparative wells 210 and the antibiotic wells 220 may be arranged in one line.

The culture line 200 includes heat appliers 230 that are disposed under the culture wells 201 and apply heat at a predetermined temperature to the culture wells 201. That is, the heat appliers 230 provide a condition suitable for culture by applying heat to the culture wells 210 and may apply heat at 35 to 40 degrees to the culture wells 201.

The preprocessing line 300 receives the sample solution S cultivated in the culture wells 201 and is composed of a plurality of preprocessing wells 301. The number of the preprocessing wells 301 may be the same as or larger than the number of the culture wells 201, and each include fluorescent particles F and magnetic particles M. That is, in the preprocessing line 300, the sample solution is transferred to the preprocessing wells 301, and the bacteria in the sample solution S, and the magnetic particles M and fluorescent particles F bond to each other. That is, the sample solution S may be injected with the magnetic particles M and fluorescent particles F preserved in the preprocessing wells 301.

The image line 400 is for planarizing the compound of the bacteria in the preprocessed sample solution S and the magnetic particles M and fluorescent particles F. The image line 400 receives the sample solution S from the preprocessing line 300, and is composed of a plurality of image wells 401 more than the culture wells 201. The magnetic member 500 is disposed under the image line 400. The compound of bacteria, magnetic particles M, and fluorescent particles F can be planarized on the bottom by the magnetism of the magnetic member 500.

The image line 400 may further include secondary fluorescent particles, which bond to a specific bacteria in the sample solution S, in the image wells 401. The secondary fluorescent particles bond to a specific bacteria, the kind of the bacteria can be identified through an analyzer 900. That is, since fluorescent particles include an aptamer or an antibody that bonds to a specific bacteria, it is possible to identify the kind of the bacteria according to the positions of the image wells 401.

The imager 600 is for imaging the fluorescent particles in image wells 401, and for example, it may be a fluorescent microscope. The imager 600 is disposed to be movable over the image wells 401, and can focus on the centers of the image wells 401 and sequentially takes images of the image wells 401. It is possible to determine an antibiotic tolerance/susceptibility on the basis of fluorescent signals of fluorescent images taken by the imager 600.

Figure 6A:
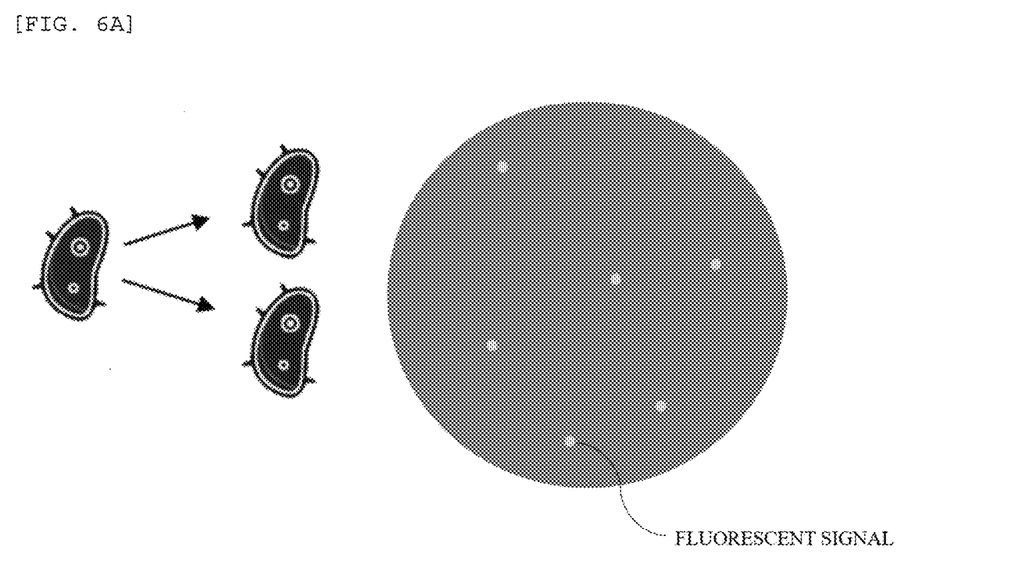
FIGS. 6A to 6C are conceptual views of fluorescent images taken by the imaging unit shown in FIG. 3.
Figure 6B:
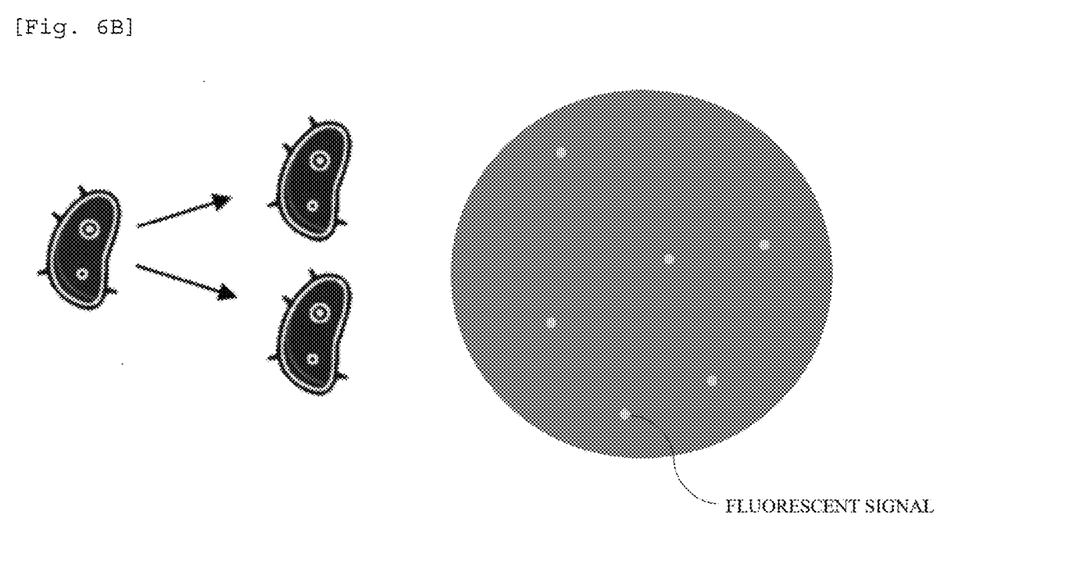
Figure 6C:
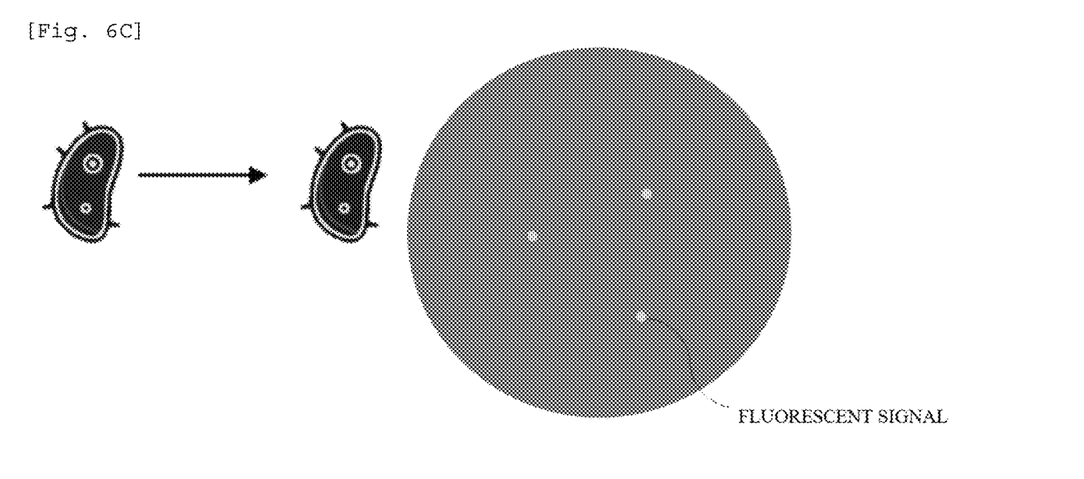

Referring to FIGS. 6A to 6C, FIG. 6A shows the fluorescent signals taken from the comparative well 210, FIG. 6B shows the fluorescent signals having an antibiotic tolerance, and FIG. 6C shows the fluorescent signals of a susceptible-to-antibiotic image well. That is, the number of fluorescent signals having an antibiotic tolerance is close to the number of the comparative wells 210, and the number of fluorescent signals having an antibiotic susceptibility is smaller than the number of the comparative wells 210. Accordingly, it is possible to quickly and accurately determine an antibiotic tolerance/susceptibility of fluorescent signals of the imager 600.

The washing line 800 is for removing the sample solution S from the image wells 401. The washing line 800 has the washing solution W and is composed of a plurality of washing wells 801 that is the same number as or more than the culture wells 201. The washing solution W in the washing line 800 may be transferred to the image wells 401 by the pipets 710.

The transfer module 700 is disposed movable over the sample solution supplier 100, the culture line 200, the preprocessing line 300, the image line 400, and the washing line 800 to transfer the sample solution S and the washing solution W. The transfer module 700 can repeatedly perform pipetting while moving the sample solution S and the washing solution by reciprocating up and down. The transfer module 700 is composed of a plurality of pipets 710 and may include a guide rail 720, a pipet frame 730, and an operation controller 740.

The guide rail 720 is installed over the sample solution supplier 100, the culture line 200, the preprocessing line 300, the image line 400, and the washing line 800. That is, the pipets 700 can transfer the sample solution S and the washing solution W to the sample solution supplier 100, the culture line 200, the preprocessing line 300, the image line 400, and the washing line 800 while moving along the guide rail 720.

The pipet frame 730 is connected to the pipets 710 and is moved with an end connected to the guide rail 720. That is, first ends of the pipets 710 are coupled to the pipet frame 730. In detail, the pipets 710 are kept in a pipet storage 701 and can be moved by the pipet frame 730 in a state coupled to the pipet frame 730. The pipets 710 can suction the sample solution S and the washing solution W through second ends thereof.

The operation controller 740 controls the pipets 710 to be able to move the sample solution S and the washing solution W, and is connected to the insides of the pipets 710. In detail, the operation controller 740 repeatedly pipets the sample solution S under a predetermined pressure, keeps an appropriate amount of sample solution S, and can transfer the sample solution S to the culture line 200, the preprocessing line 300, the image line 400, and the washing line 800.

The analyzer 900 automatically determines an antibiotic tolerance/susceptibility by receiving fluorescent images taken by the imager 600 and analyzing fluorescent signals. The analyzer 900 can find out the number of the fluorescent signals of the fluorescent images taken by the imager 600 and detect the fluorescent signals through a digital fluorescence counting technology using an image processing algorithm. The analyzer 900 can determine an antibiotic tolerance/susceptibility of the sample solution S on the basis of the number of fluorescent signals analyzed through the digital fluorescence counting technology. In detail, the image analyzing step S600A can distinguish (a) the comparative well 210 and a tolerance well or (b) a susceptibility well in accordance with the number of the fluorescent signals. When the number of the fluorescent signals of the susceptibility wells is 15% larger than the standard deviation/average of the number of the fluorescent signals in the comparative wells 210 and the tolerance wells, an antibiotic susceptibility is determined to be present. When the number of the fluorescent signals in the comparative wells 210 and the tolerance wells is within 15% of the standard deviation/average, an antibiotic tolerance is determined to be present. When errors during the operation and imaging are partially sensed, the corresponding well might be determined as one having an antibiotic tolerance. The analyzer 900 can detect the fluorescent signals of secondary fluorescent particles bonding to a specific bacterium. That is, the analyzer 900 can identify the kind of bacteria according to the positions of the image wells 401 by detecting secondary fluorescent particle signals.

The culture line 200, the preprocessing line 300, the image line 400, and the washing line 800 may be configured in one cartridge well. The apparatus 10 for testing an antibiotic susceptibility, which is an automated apparatus, can receive a quick and accurate antibiotic tolerance/susceptibility test result using a simple configuration.

The method S10 and apparatus 10 for testing an antibiotic susceptibility according to the present disclosure can determine whether bacteria propagate, which depends on whether the bacteria have an antibiotic tolerance/susceptibility, in the unit of cell through fluorescent images, so it is possible to more quickly derive a result than existing methods that require a long culture time.

Further, the method and apparatus digitize the propagation level of microorganisms, which depends on antibiotics, through fluorescent images, so it is possible to derive an accurate result. Further, the method and apparatus can selectively perform determination for microorganism identification using secondary fluorescent substances that can bond to a specific bacterium.

Further, the apparatus for testing an antibiotic susceptibility can replace professional manpower because it is an automated testing apparatus, the use efficiency is high.

Although the present disclosure has been described with reference to the exemplary embodiments illustrated in the drawings, those are only examples and may be changed and modified into other equivalent exemplary embodiments from the present disclosure by those skilled in the art. Therefore, the technical protective region of the present disclosure should be determined by the scope described in claims.

What is claimed is:

1. A method of testing an antibiotic susceptibility, the method comprising:
    a cultivating step of dispensing and cultivating sample solution into culture wells including one or more comparative wells and a plurality of antibiotic wells receiving two or more kinds of antibiotics, respectively;
    a preprocessing step of receiving the sample solution, which has been cultivated in the cultivating step, into a plurality of preprocessing wells each including magnetic particles and fluorescent particles that bond to one or more kinds of bacteria such that the bacteria and the magnetic particles and fluorescent particles bond to each other;
    a planarizing step of receiving the sample solution, which has undergone the preprocessing step, into a plurality of image wells having magnetic members thereunder such that the magnetic particles bonding to the bacteria are arranged on the bottoms of the image wells;
    a washing step of removing the sample solution from the image wells that have undergone the planarizing step;
    an imaging step of taking fluorescent images of the image wells washed in the washing step; and an analyzing step of determining an antibiotic tolerance/susceptibility of the sample solution by analyzing the fluorescent images taken in the imaging step.

2. The method of claim 1, further comprising a sample homogenizing step of homogenizing the sample solution by repeatedly pipetting the sample solution using a plurality of pipets.

3. The method of claim 1, wherein the cultivating step includes a culture heat applying step of applying heat at 35 to 40 degrees to the culture wells, and
cultivates the sample solution dispensed in the culture wells for 60 to 90 minutes.

4. The method of claim 1, comprising:
a primary transfer step of transferring the sample solution cultivated in the culture wells to the preprocessing wells using a plurality of pipets; and
a secondary transfer step of transferring the sample solution in the preprocessing wells to the image wells, respectively, using the pipets.

5. The method of claim 1, wherein the washing includes:
a sample solution removal step of removing top sample solution in the image wells that have undergone the planarizing; and
a washing solution supply step of supplying washing solution from a plurality of washing wells having washing solution to the image wells with the top sample solution removed through the sample solution removal step.

6. The method of claim 1, wherein the analyzing step includes:
an image analyzing step of finding out the number of fluorescent signals of fluorescent images taken in the imaging step; and
an antibiotic analyzing step of determining an antibiotic tolerance/susceptibility of the sample solution on the basis of the number of the fluorescent signals analyzed in the image analyzing step.

7. The method of claim 1, further comprising a specific bacteria-fluorescence bonding step of bonding the bacteria in the sample solution to secondary fluorescent particles.

8. An apparatus for testing an antibiotic susceptibility, the apparatus comprising:
a sample solution supplier;
a culture line composed of three or more rows of culture wells that receive sample solution from the sample solution supplier and include one or more comparative wells and a plurality of antibiotic wells having two or more antibiotics, respectively;
a preprocessing line composed of a plurality of preprocessing wells that receives sample solution cultivated in the culture wells, is provided in the same number as or more than the culture wells, and each has fluorescent particles and magnetic particles;
an image line composed of a plurality of image wells that receives the sample solution in the preprocessing line and is provided in the same number as or more than the culture wells;
a magnetic member disposed under the image line; and
an imager imaging the fluorescent particles in the image wells.

9. The apparatus of claim 8, comprising a transfer module disposed to be movable over the sample solution supplier, the culture line, the preprocessing line, and the image line, and composed of a plurality of pipets moving sample solution by reciprocating up and down.

10. The apparatus of claim 9, wherein the transfer module includes:
a guide rail installed over the sample solution supplier, the culture line, the preprocessing line, and the image line;
a pipet frame moving with an end coupled to the guide rail;
a plurality of pipets having a first end coupled to the pipet frame and a second end receiving sample solution; and
an operation controller connected to the insides of the pipets and moving sample solution under predetermined pressure.

11. The apparatus of claim 8, wherein the culture line includes a heat applier disposed under the culture wells and applying culture heat at a predetermined temperature to the culture wells.

12. The apparatus of claim 8, further comprising a washing line composed of a plurality of washing wells having washing solution to be transferred to the image wells, respectively, and provided in the same number as or more than the culture wells.

* * * * *